US008461300B2

(12) United States Patent
Robinson et al.

(10) Patent No.: US 8,461,300 B2
(45) Date of Patent: Jun. 11, 2013

(54) MATERIALS AND METHODS FOR STABILIZING NANOPARTICLES IN SALT SOLUTIONS

(75) Inventors: David Bruce Robinson, Fremont, CA (US); Ronald Zuckermann, El Cerrito, CA (US); George M. Buffleben, Tracy, CA (US)

(73) Assignee: Sandia Corporation, Albuquerque, NM (US)

( * ) Notice: Subject to any disclaimer, the term of this patent is extended or adjusted under 35 U.S.C. 154(b) by 70 days.

(21) Appl. No.: 13/005,250

(22) Filed: Jan. 12, 2011

(65) Prior Publication Data
US 2011/0230427 A1 Sep. 22, 2011

Related U.S. Application Data

(60) Provisional application No. 61/316,232, filed on Mar. 22, 2010, provisional application No. 61/318,897, filed on Mar. 30, 2010, provisional application No. 61/394,951, filed on Oct. 20, 2010.

(51) Int. Cl.
*A61K 38/00* (2006.01)
(52) U.S. Cl.
USPC ............................ 530/333; 514/336; 514/337
(58) Field of Classification Search
None
See application file for complete search history.

(56) References Cited

U.S. PATENT DOCUMENTS

| | | | |
|---|---|---|---|
| 5,831,005 A | 11/1998 | Zuckerman |
| 6,759,387 B2 | 7/2004 | Rothbard |
| 7,030,216 B2 | 4/2006 | Horn |
| 7,408,023 B2 | 8/2008 | Horn |
| 2004/0038406 A1 | 2/2004 | Unger |
| 2008/0213377 A1 | 9/2008 | Bhatia |
| 2009/0226528 A1 | 9/2009 | Czech |

OTHER PUBLICATIONS

Levy et al., Rational and Combinatorial Design of Peptide Capping Ligands for Gold Nanoparticles, Journal of the American Chemical Society, 2004, v. 126(32): 10076-10084.*
Langham et al. (Poster Session, Peptoids are versatile, tunable surfactants that stabilize nanoparticles, Colloids Surfaces, San Francisco, (Mar. 21-24, 2010).*
Sanborn et al. (Extreme Stability of Helices Formed by Water-Soluble Poly-N-Substituted Glycines (polypeptoids) with α-Chiral Side Chains, Biopolymers, vol. 63, p. 12-20 (2002).*
Horn et al., (Bioconjugate Chem., vol. 15, p. 428-435 (2004).*
Levy et al., "Rational and Combinatorial Design of Peptide Capping Ligands for Gold Nanoparticles," Journal of the American Chemical Society, 2004, v. 126(32): 10076-10084.*
Sanborn et al., Extreme Stability of Helices Formed by Water-Soluble Poly-N-Substituted Glycines (polypeptoids) with α-Chiral Side Chains, Biopolymers, vol. 63, p. 12-20 (2002).*
Horn et al., Bioconjugate Chem., vol. 15, p. 428-435 (2004).*
Bain, C. D.; Biebuyck, H. A.; Whitesides, G. M., "Comparison of Self-Assembled Monolayers on Gold: Coadsorption of Thiols and Disulfides," Langmuir, 1989, v.5(3): 723-727.
Bain, C. D.; Troughton, E. B.; Tao, Y. T.; Evall, J.; Whitesides, G. M.; Nuzzo, R. G. "Formation of monolayer films by the spontaneous assembly of organic thiols from solution onto gold," Journal of the American Chemical Society, 1989, v.111(1): 321-335.
Barish, R. D.; Schulman, R.; Rothemund, P. W. K.; Winfree, E., "An information-bearing seed for nucleating algorithmic self-assembly," Proceedings of the National Academy of Science, 2009, v.106(15): 6054-6059.
Busbee, B. D.; Obare, S. O.; Murphy, C. J., "An improved synthesis of high-aspect-ratio gold nanorods," Advanced Materials, 2003, v.15(5): 414-416.
Chidsey, C. E. D.; Loiacono, D. N. "Chemical Functionality in Self-Assembled Monolayers: Structural and Electrochemical Properties," Langmuir, 1990, v.6(3): 682-691.
Claridge, S. A.; Liang, H. Y. W.; Basu, S. R.; Frechet, J. M. J.; Alivisatos, A. P. "Isolation of Discrete Nanoparticle-DNA Conjugates for Plasmonic Applications," Nano Letters, 2008, v.8(4): 1202-1206.
Clegg, R. S.; Hutchison, J. E. "Control of monolayer assembly structure by hydrogen bonding rather than by adsorbate-substrate templating," Journal of the American Chemical Society, 1999, v.121(22): 5319-5327.
Ding, B. Q.; Deng, Z. T.; Yan, H.; Cabrini, S.; Zuckermann, R. N.; Bokor, J. "Gold Nanoparticle Self-Similar Chain Structure Organized by DNA Origami," Journal of the American Chemical Society, 2010, v.132(10): 3248-3249.
Doty, R. C.; Tshikhudo, T. R.; Brust, M.; Fernig, D. G. "Extremely Stable Water-Soluble Ag Nanoparticles," Chemistry of Materials, 2005, v.17(18): 4630-4635.
Duchesne, L.; Gentili, D.; Comes-Franchini, M.; Fernig, D. G. "Robust Ligand Shells for Biological Applications of Gold Nanoparticles," Langmuir, 2008, v.24(23): 13572-13580.
Figliozzi, G. M.; Goldsmith, R.; Ng, S. C.; Banville, S. C.; Zuckermann, R. N. "Synthesis of N-substituted glycine peptoid libraries," Methods in Enzymology, 1996, v.267: 437-447.
Frens, G. "Controlled Nucleation for Regulation of Particle Size in Monodisperse Gold Suspensions," Nature-Physical Science, 1973, v.241(105): 20-22.
Giljohann, D. A.; Seferos, D. S.; Prigodich, A. E.; Patel, P. C.; Mirkin, C. A. "Gene regulation with polyvalent with siRNA-nanoparticle conjugates," Journal of the American Chemical Society, 2009, v.131(6): 2072-2073.
Gorske, B. C.; Stringer, J. R.; Bastian, B. L.; Fowler, S. A.; Blackwell, H. E. "New Strategies for the Design of Folded Peptoids Revealed by a Survey of Noncovalent Interactions in Model Systems," Journal of the American Chemical Society, 2009, v.131(45): 16555-16567.

(Continued)

*Primary Examiner* — Cecilia J Tsang
*Assistant Examiner* — Randall L Beane
(74) *Attorney, Agent, or Firm* — Timothy P. Evans

(57) ABSTRACT

Sequence-specific polymers are proving to be a powerful approach to assembly and manipulation of matter on the nanometer scale. Ligands that are peptoids, or sequence-specific N-functional glycine oligomers, allow precise and flexible control over the arrangement of binding groups, steric spacers, charge, and other functionality. We have synthesized short peptoids that can prevent the aggregation of gold nanoparticles in high-salt environments including divalent salt, and allow co-adsorption of a single DNA molecule. This degree of precision and versatility is likely to prove essential in bottom-up assembly of nanostructures and in biomedical applications of nanomaterials.

3 Claims, 8 Drawing Sheets

OTHER PUBLICATIONS

Hicks, J. F.; Miles, D. T.; Murray, R. W. "Quantized double-layer charging of highly monodisperse metal nanoparticles," Journal of the American Chemical Society, 2002, v.124(44): 13322-13328.

Jana, N.R.; Gearheart, L.; Murphy, C.J, "Wet chemical synthesis of high aspect ratio cylindrical gold nanorods," Journal of Physical Chemistry B, 2001, v.105(19): pp. 4065-4067.

Jungmann, R.; Liedl, T.; Sobey, T. L.; Shih, W.; Simmel, F. C. "Isothermal assembly of DNA origami structures using denaturing agents," Journal of the American Chemical Society, 2008, v.130(31): 10062-10063.

Kirshenbaum, K., Barron, A.E., Goldsmith, R.A., Armand, P., Bradley, E.K., Truong, K.T.V., Dill, K. A., Cohen, F.E., Zuckermann, R.N., "Sequence-specific polypeptoids: A diverse family of heteropolymers with stable secondary structure," Proceedings of the National Academy of Science of the United States of America, 1998, v95(8): 4303-4308.

Lee, S. E.; Liu, G. L.; Kim, F.; Lee, L. P.,"Remote Optical Switch for Localized and Selective Control of Gene Interference," Nano Letters, 2009, v.9(2): 562-570.

Leff, D. V.; Brandt, L.; Heath, J. R., "Synthesis and Characterization of Hydrophobic, Organically-Soluble Gold Nanocrystals Functionalized with Primary Amines," Langmuir, 1996, v.12(20): 4723-4730.

Levy, R.; Thanh, N. T. K.; Doty, R. C.; Hussain, I.; Nichols, R. J.; Schiffrin, D. J.; Brust, M.; Fernig, D. G. "Rational and Combinatorial Design of Peptide Capping Ligands for Gold Nanoparticles," Journal of the American Chemical Society, 2004, v.126(32): 10076-10084.

Loweth, C. J.; Caldwell, W. B.; Peng, X. G.; Alivisatos, A. P.; Schultz, P. G. "DNA-Based Assembly of Gold Nanocrystals," Angewandte Chemie International Edition, 1999, v.38(12): 1808-1812.

Ma, H. L.; Xu, Y. F.; Qi, X. R.; Maitani, Y.; Nagai, T., "Superparamagnetic iron oxide nanoparticles stabilized by alginate: Pharmacokinetics, tissue distribution, and applications in detecting liver cancers," International Journal of Pharmaceutics, 2008, v.354(1-2): 217-226.

Mastroianni, A. J.; Claridge, S. A.; Alivisatos, A. P. "Pyramidal and Chiral Groupings of Gold Nanocrystals Assembled Using DNA Scaffolds," Journal of the American Chemical Society, 2009, v.131(24): 8455-8459.

Mühlpfordt, H. "The preparation of colloidal gold particles using tannic-acid as an additional reducing agent," Experientia, 1982, v.38(9): 1127-1128.

Nykypanchuk, D.; Maye, M. M.; Van Der Lelie, D.; Gang, O., "DNA-guided crystallization of colloidal nanoparticles," Nature, 2008, v.451(7178): 549-552.

Porter, M. D.; Bright, T. B.; Allara, D. L.; Chidsey, C. E. D. "Spontaneously organized molecular assemblies .4. Structural characterization of normal-alkyl thiol monolayers on gold by optical ellipsometry, infrared-spectroscopy, and electrochemistry," Journal of the American Chemical Society, 1987, v.109(12): 3559-3568.

Porter, L. A.; Ji, D.; Westcott, S. L.; Graupe, M.; Czernuszewicz, R. S.; Halas, N. J.; Lee, T.R., "Gold and Silver Nanoparticles Functionalized by the Adsorption of Dialkyl Disulfides," Langmuir, 1998, v.14(26): 7378-7386.

Rothemund, P. W. K.; Ekani-Nkodo, A.; Papadakis, N.; Kumar, A.; Fygenson, D. K.; Winfree, E. "Design and characterization of programmable DNA nanotubes," Journal of the American Chemical Society, 2004, v.126(50): 16344-16352.

Rothemund, P. W. K., "Folding DNA to create nanoscale shapes and patterns," Nature, 2006, v.440(7082): 297-302.

Sanborn, T. J.; Wu, C. W.; Zuckerman, R. N.; Barron, A. E. "Extreme Stability of Helices Formed by Water Soluble Poly-N-Substituted Glycines (Polypeptoids) with α-Chiral Side Chains," Biopolymers, 2002, v.63(1): 12-20.

Sau, T.K., Murphy, C.J., "Seeded High Yield Synthesis of Short Au Nanorods in Aqueous Solution," Langmuir, 2004, v20(15): 6414-6420.

Schmid, G.; Lehnert, A., "The Complexation of Gold Colloids," Angewandte Chemie International Edition, 1989, v.28(6): 780-781.

Schulman, R.; Winfree, E., "Synthesis of crystals with a programmable kinetic barrier to nucleation," Proceedings of the National Academy of Science, 2007, v.104(39): 15236-15241.

Sharma, J.; Chhabra, R.; Andersen, C. S.; Gothelf, K. V.; Yan, H.; Liu, Y. "Toward reliable gold nanoparticle patterning on self-assembled DNA nanoscaffold," Journal of the American Chemical Society, 2008, v.130(25): 7820-7821.

Sharma, J.; Chhabra, R.; Cheng, A.; Brownell, J.; Liu, Y.; Yan, H. "Control of Self-Assembly of DNA Tubules Through Integration of Gold Nanoparticles," Science, 2009, v.323(5910): 112-116.

Slot, J. W.; Geuze, H. J. "A new method of preparing gold probes for multiple-labeling ctyo-chemistry" European Journal of Cell Biology, 1985, v.38(1): 87-93.

Sui, Q.; Borchardt, D.; Rabenstein, D. L. "Kinetics and equilibria of cis/trans isomerization of backbone amide bonds in peptoids," Journal of the American Chemical Society, 2007, v.129(39): 12042-12048.

Troughton, E. B.; Bain, C. D.; Whitesides, G. M.; Nuzzo, R. G.; Allara, D. L.; Porter, M. D., "Monolayer Films Prepared by the Spontaneous Self-Assembly of Symmetrical and Unsymmetrical Dialkyl Properties, and Reactivity of Constituent Functional Sulfides from Solution onto Gold Substrates: Structure, Group," Langmuir, 1988, v.4(2): 365-385.

Wen, Y. Q.; McLaughlin, C. K.; Lo, P. K.; Yang, H.; Sleiman, H. F. "Stable Gold Nanoparticle Conjugation to Internal DNA Positions: Facile Generation of Discrete Gold Nanoparticle-DNA Assemblies," Bioconjugate Chemistry, 2010, v.21(8): 1413-1416.

Wu, C. W.; Sanborn, T. J.; Huang, K.; Zuckermann, R. N.; Barron, A. E. "Peptoid oligomers with alpha-chiral, aromatic side chains: Sequence requirements for the formation of stable peptoid helices," Journal of the American Chemical Society, v.123(28): 6778-6784 (Jul. 18, 2001).

Wu, C. W.; Sanborn, T. J.; Zuckermann, R. N.; Barron, A. E. "Peptoid oligomers with alpha-chiral, aromatic side chains: Effects of chain length on secondary structure," Journal of the American Chemical Society, 2001, v.123(13): 2958-2963.

Yamauchi, Y., Yokoshima, T., Momma, T., Osaka, T., Kuroda, K. "Fabrication of magnetic mesostructured nickel-cobalt alloys from lyotropic liquid crystalline media by electroless deposition," Journal of Materials Chemistry, 2004, v14(19): 2934-2940.

Zanchet, D.; Micheel, C. M.; Parak, W. J.; Gerion, D.; Alivisatos, A. P. "Electrophoretic Isolation of Discrete Au Nanocrystal/DNA Conjugates Nano Letters," Nano Letters, 2001, v.1(1): 32-35.

Zhang, C. A.; He, Y.; Su, M.; Ko, S. H.; Ye, T.; Leng, Y. J.; Sun, X. P.; Ribbe, A. E.; Jiang, W.; Mao, C. D., "DNA self-assembly: from 2D to 3D," Faraday Discussions, 2009, v.143: 221-233.

Zheng, J. W.; Lukeman, P. S.; Sherman, W. B.; Micheel, C.; Alivisatos, A. P.; Constantinou, P. E.; Seeman, N. C. "Metallic Nanoparticles Used to Estimate the Structural Integrity of DNA Motifs ," Biophysical Journal, 2008, v.95(7): 3340-3348.

Zuckermann, R.N., Kerr, J.M., Kent, S.B.H., Moost, W.H.; "Efficient Method for the Preparation of Peptoids [Oligo(N-substituted glycines)] by Submonomer Solid-Phase Synthesis," Journal of the American Chemical Society. 1992, v.114(26):10646-10647.

\* cited by examiner

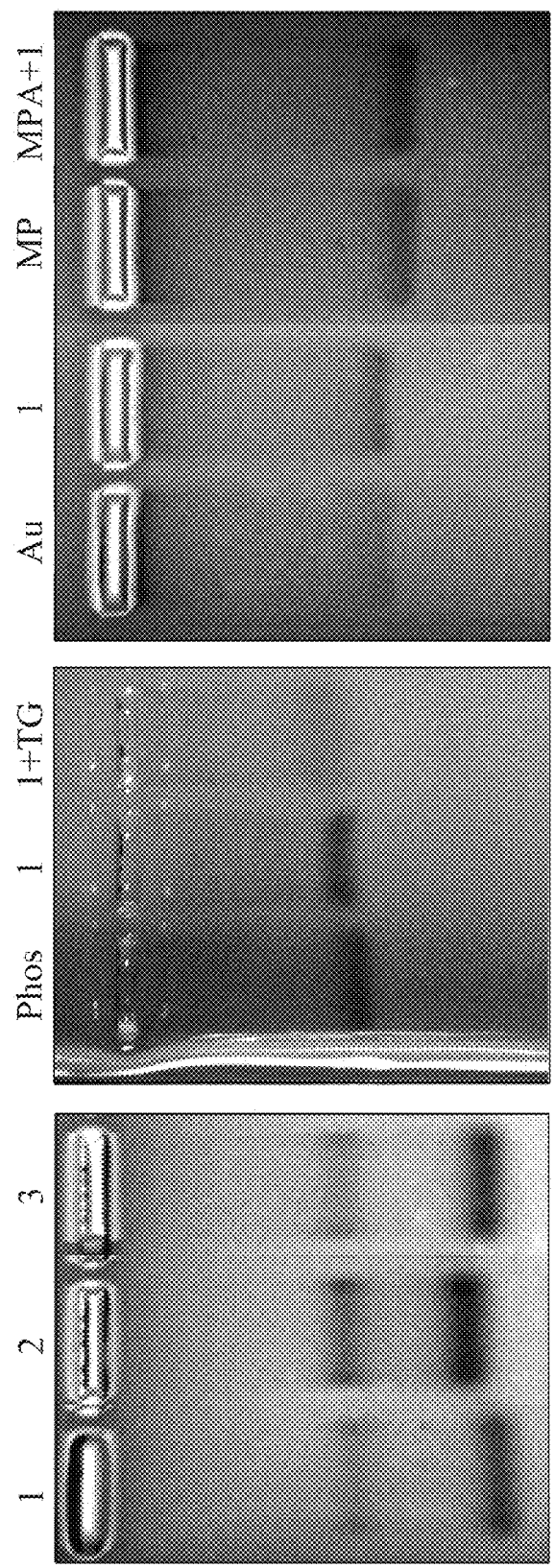

MATERIALS AND METHODS FOR STABILIZING NANOPARTICLES IN SALT SOLUTIONS

CROSS REFERENCE TO RELATED APPLICATION(S)

This application claims the benefit of the filing date of U.S. Provisional Applications 61/316,232 and 61/318,897, filed respectively on Mar. 22, 2010 and Mar. 30, 2010 both entitled "Sequence-Specific Oligomers to Stabilize Nanoparticles in Aqueous Solutions of Metal Salts" and the filing date of U.S. Provisional Application 61/394,951, filed on Oct. 20, 2010 entitled "Stabilization of Nanoparticles under Biological Assembly Conditions using Peptoids." Each of the aforementioned provisional applications is hereby incorporated by reference, in its entirety, for all purposes.

STATEMENT OF GOVERNMENT INTEREST

This invention was made with Government support under Government Contract No. DE-AC04-94AL85000 awarded by the U.S. Department of Energy to Sandia Corporation. Portions of this work were performed at the Molecular Foundry, Lawrence Berkeley National Laboratory, which is supported by the Office of Science, Office of Basic Energy Sciences, U.S. Department of Energy, under Contract No. DE-AC02-05CH11231. The Government has certain rights in the invention, including a paid-up license and the right, in limited circumstances, to require the owner of any patent issuing in this invention to license others on reasonable terms.

FIELD OF THE INVENTION

The present invention broadly relates to a process for organizing nanoparticles in artificial structures which comprise materials having increased tolerance for biological environments such as blood or cytoplasm for use in medical and/or drug delivery applications, or for conditions in which biological macromolecules are used for assembly and fabrication of nanostructures. More particularly, the invention relates to organizing stable, aqueous suspensions of nanoparticles, wherein the aqueous media comprises monovalent salt at any concentration up to saturation and multivalent salts up to concentrations on the order of one hundred millimolar multivalent cations.

BACKGROUND

The artificial organization of inorganic material into designed structures on the nanometer scale is a fundamental technological problem. Photolithography, the predominant technique, is used primarily to achieve high-density information storage and processing. Further mastery of architectures on this length scale may advance these goals and create new realms of application, such as a general approach to interfaces with single biomolecules or organelles.

Sequence-specific polymers are a promising pathway toward the goal of artificial organization of inorganic material, as demonstrated by the DNA origami technique, in which a long single strand of DNA is folded into elaborate patterns using short oligomers that connect different parts of the long strand. These structures have been formed into tiles and tubes in various forms demonstrating the versatility and generality of the method. Others have used the assembly properties of DNA to precisely organize inorganic nanoparticles in periodic or chiral structures (Nykypanchuk, D.; Maye, M. M.; van der Lelie, D.; Gang, O. "DNA-guided crystallization of colloidal nanoparticles," *Nature*, 2008, v. 451, 549-552; Mastroianni, A. J.; Claridge, S. A.; Alivisatos, A. P. "Pyramidal and Chiral Groupings of Gold Nanocrystals Assembled Using DNA Scaffolds," *Journal of the American Chemical Society*, 2009, v. 131 (24): 8455-8459). Gold nanoparticles have been incorporated into DNA origami and other nucleic acid nanostructures with high precision, but not with high generality, requiring constraints on the templating structure, the use of specific particle sizes, or requiring coatings that are thick with respect to inorganic particle size (Ding, B. Q.; Deng, Z. T.; Yan, H.; Cabrini, S.; Zuckermann, R. N.; Bokor, J. "Gold Nanoparticle Self-Similar Chain Structure Organized by DNA Origami," *Journal of the American Chemical Society*, 2010, v. 132 (10): 3248-3249; Sharma, J.; Chhabra, R.; Cheng, A.; Brownell, J.; Liu, Y.; Yan, H. "Control of Self-Assembly of DNA Tubules Through Integration of Gold Nanoparticles," *Science*, 2009, v. 323 (5910): 112-116; Zheng, J. W.; Lukeman, P. S.; Sherman, W. B.; Micheel, C.; Alivisatos, A. P.; Constantinou, P. E.; Seeman, N. C. "Metallic Nanoparticles Used to Estimate the Structural Integrity of DNA Motifs," *Biophysical Journal*, 2008, v. 95 (7): 3340-3348; Wen, Y. Q.; McLaughlin, C. K.; Lo, P. K.; Yang, H.; Sleiman, H. F. "Stable Gold Nanoparticle Conjugation to Internal DNA Positions: Facile Generation of Discrete Gold Nanoparticle—DNA Assemblies," *Bioconjugate Chemistry*, 2010, v. 21 (8): 1413-1416).

One factor likely to limit the generality of assembly of inorganic materials using DNA, or their subsequent application in biological environments, is the need for using a divalent salt in concentration levels of at least tens of millimolar (mM) during assembly and manipulation of compact DNA nanostructures. This is especially true in the case of DNA origami, where tightly folded strands create high densities of negatively charged phosphate ions. In contrast, inorganic nanoparticles typically benefit from the effect of inter-particle electrostatic repulsion for stability against particle aggregation. However, increased salt concentration weakens this repulsive effect and divalent salts can also have a crosslinking effect as noted by Elimelech, et al., (*Particle Deposition & Aggregation: Measurement, Modeling and Simulation*; Butterworth-Heinemann: Oxford, 1998). Thick surfactant or polymer coatings on particles can mitigate this effect but use of such coatings may also mask the function of the inorganic material, limit the precision and pitch of positions on a template, and limit transport and uptake in biological environments.

For functionalizing gold nanoparticles with DNA, a small anionic ligand, bis (p-sulfonato) triphenylphosphine, is often used because it is a small molecule that is easily displaced by thiolated functional molecules and one that has low nonspecific binding to DNA and other materials. However, bis (p-sulfonato) triphenylphosphine provides no tolerance to even relatively low concentrations (e.g. ~1 mM) of magnesium solute cation.

Another strategy is to completely encapsulate nanoparticles with thiolated DNA, in some cases applying a small number of long strands along with a large number of shorter oligomers (op. cit., D. Nykypanchuk; B. Q. Ding; and J. Sharma). This modification confers some magnesium ion tolerance together with some loss of the advantages of the phosphine. However, they also perturb DNA nanostructures: their structure in the presence of particles is very different from their structure in the absence of these particles (op. cit. Yan, H., et al. *Science*, 2009, v. 323 (5910): 112-116). This is not surprising given that the total charge on the functionalized gold particle is high, and not widely tunable.

Greater versatility may be obtained by using other sequence-specific polymers, with a wider range of functionality, as ligands. Short oligo-peptides have been designed by Fernig et al. that confer monovalent salt tolerance in the high hundreds of mM, although any tests of these in the presence of magnesium salts and/or DNA have not been reported (see Levy, R.; Thanh, N. T. K.; Doty, R. C.; Hussain, I.; Nichols, R. J.; Schiffrin, D. J.; Brust, M.; Fernig, D. G. "Rational and Combinatorial Design of Peptide Capping Ligands for Gold Nanoparticles," *Journal of the American Chemical Society,* 2004, v. 126 (32): 10076-10084; Doty, R. C.; Tshikhudo, T. R.; Brust, M.; Fernig, D. G., "Extremely Stable Water-Soluble Ag Nanoparticles," *Chemistry of Materials,* 2005, v. 17 (18): 4630-4635; and Duchesne, L.; Gentili, D.; Comes-Franchini, M.; Fernig, D. G. "Robust Ligand Shells for Biological Applications of Gold Nanoparticles," *Langmuir,* 2008, v. 24 (23): 13572-13580). Oligo-N-functional glycines (also known as "peptoids") have conformations that are less salt-dependent than similar peptides, and it was posited that this may confer function that is also less salt-dependent.

U.S. Pat. Nos. 6,306,993 and 6,759,387 disclose methods and compositions for transporting drugs and macromolecules across biological membranes. The invention includes a method for enhancing transport of a compound across a biological membrane, wherein a biological membrane is contacted with a conjugate containing a biologically active agent that is covalently attached to a transport polymer consisting of 6 to 25 subunits, at least 50% of which contain a guanidino- or an amidino-sidechain moiety. The latter also discloses polymers that include, for example, poly-arginine molecules that are preferably between about 6 and 25 residues in length.

U.S. Pat. No. 7,427,600 provides covalent attachment of active agents to a peptide. The invention may be distinguished from the above mentioned technologies by virtue of covalently attaching the active agent directly, which includes, for example, pharmaceutical drugs and nutrients, to the N-terminus, the C-terminus or to the side chain of an amino acid, an oligopeptide or a polypeptide, also referred to herein as a carrier peptide. In another embodiment, when the active agent is itself an amino acid active agent, then the active agent may be part of the chain at either the C-terminus or N-terminus through a peptide bond, or interspersed in the polypeptide via peptide bonds on both sides of the active agent. In another embodiment, the peptide stabilizes the active agent, primarily in the stomach, through conformational protection. In this application, delivery of the active agent is controlled, in part, by the kinetics of unfolding of the carrier peptide. Upon entry into the upper intestinal tract, indigenous enzymes release the active ingredient for absorption by the body by hydrolyzing the peptide bonds of the carrier peptide. This enzymatic action introduces the second phase of the sustained release mechanism.

Published U.S. Pat. Appln. No. 20070098713 discloses the use of small particles in biological systems, including the delivery of biologically active agents. Some embodiments relate to a collection of particles having an agent, a surfactant molecule having an HLB value of less than about 6.0 units, and a polymer, wherein the collection of particles has an average diameter of less than about 100 nanometers, wherein the agent is a protein, carbohydrate, polypeptide, adjuvant, nucleic acid encoding a protein, a visualization agent, or a marker.

Similarly, published U.S. Pat. Appln. No. 20080213377 discloses systems, methods, and compositions for targeted delivery of nanoparticles and/or agents to tissues, cells, and/or subcellular locales. In general, compositions comprise a nanoparticle (e.g. quantum dot, polymeric particle, etc.), at least one modulating entity (such as a targeting moiety, transfection reagent, protective entity, etc.), and at least one agent to be delivered (e.g. therapeutic, prophylactic, and/or diagnostic agent). The present invention provides methods of making and using nanoparticle entities in accordance with the present invention.

In addition, U.S. Pat. Appln. No. 20090226528 discloses methods and compositions for delivering payload molecules, including nucleic acids, using yeast cell wall particles. Embodiments of the invention are useful for delivering a variety of molecules to cells. Aspects of the invention include yeast cell wall particles encapsulating nanoparticles comprising payload molecules.

SUMMARY

In this work, we describe several peptoids that stabilize 5 nm and 10 nm gold particles in solutions comprising high concentrations of monovalent salt, and moderate concentrations of divalent salt, and show that their interaction with thiolated DNA is similar to that of bis (p-sulfonato) triphenylphosphine ("phosphine" or "phosphine ligand"). This constitutes another strategy to facilitate DNA-nanoparticle interactions in nucleic acid nanostructures that may prove useful in biomedical applications of gold nanoparticles such as in gene delivery.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods and devices disclosed herein. In the drawings:

FIG. 3A shows electrophoresis of treated 5 nm gold particles in a 2% agarose gel, in 0.5×TBE buffer, wherein particles protected with peptoids 1-3 were acid-precipitated and re-dispersed in the TBE buffer.

FIG. 3B shows electrophoresis of treated particles in a 0.8% agarose gel, wherein the lane labeled "Phos." comprises phosphine-treated (Phos) particles; wherein the lane labeled "1" comprises peptoid 1-treated particles; and wherein the lane labeled "1+TG" comprises peptoid 1-treated particles that were subsequently treated with a comparable molar amount of thioglycerol (TG) several hours later, wherein the gold particles were concentrated by salt precipitation.

FIG. 3C shows electrophoresis of suspensions of gold particles in a 3% agarose gel, wherein the lane labeled "Au" comprises a suspension of commercial colloidal gold; wherein the lane labeled "1" comprises peptoid 1-protected gold particles; wherein the lane labeled "MPA" comprises mercaptopropionate-protected gold; and wherein the lane labeled "MPA+P1" comprises mercaptopropionate and peptoid 1-protected gold particles, wherein the gold particles were concentrated by salt precipitation.

DETAILED DESCRIPTION OF VARIOUS EMBODIMENTS OF THE INVENTION

Figure 1:
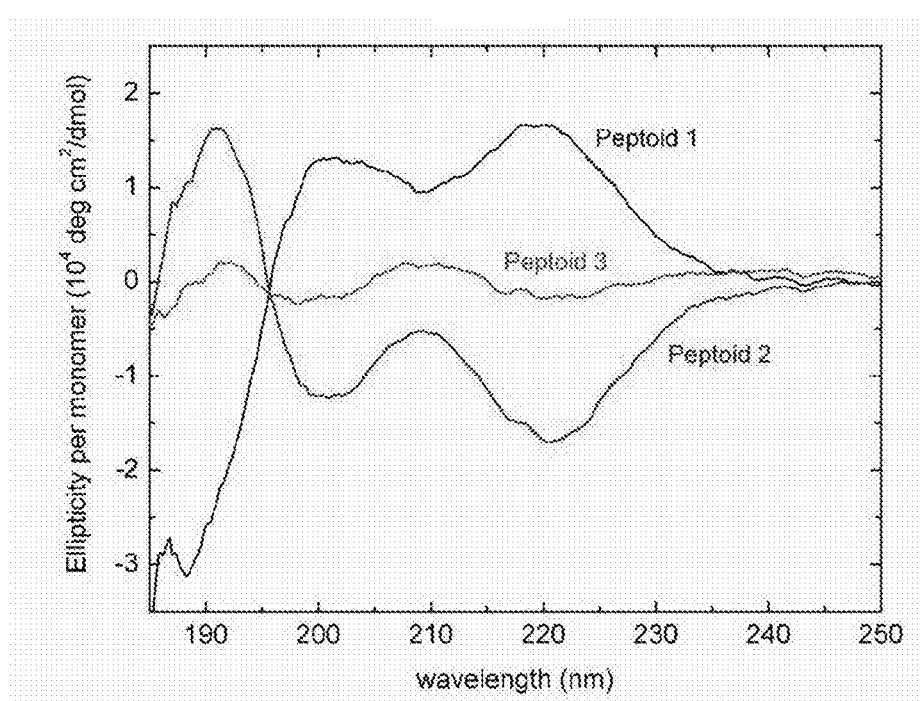
FIG. 1 shows circular dichroism spectra of peptoids 1-3 listed in TABLE 1 from stock solutions diluted to 50 g/mL at room temperature.

Aqueous suspensions of inorganic nanoparticles generally hold a net charge, and their stability in water with respect to aggregation is strongly dependent on the concentration of solute salts, and especially multivalent salts. Moreover, sequence-specific N-functional glycine oligomers, also known as "peptoids," are a class of materials that can be used as nanoparticle ligands with precisely defined length and chemical functionality. We have designed and synthesized such ligands, and demonstrated several that stabilize nanoparticles comprising gold or a coating of gold in aqueous solutions comprising tens of millimolar concentrations of $Mg^{+2}$ cation and/or hundreds of millimolar concentrations of $Na^+$ cation. Furthermore, we believe that our design is applicable to any nanoparticle comprising a surface material to which a sulfur moiety will bind preferentially to ligands present on the particle as a result of a previous process.

EXAMPLES

Peptoid Synthesis: Peptoids were synthesized according to standard procedures such as those described by Figliozzi, et al., ("Synthesis of N-substituted glycine peptoid libraries," *Methods in Enzymology*, 1996, v. 267: 437-447), herein incorporated by reference, in its entirety, for all purposes. Our procedure utilized either an Apex 396 Automated Peptide Synthesizer (available from AAPPTec, LLC, Louisville, Ky.) or a customized programmable syringe pump (available from J-Kem Scientific, Inc., Saint Louis, Mo.) with multiport valves for reagent selection and solenoid valves to apply nitrogen pressure for bubbling or draining a fritted reaction tube. Reagent chemicals were obtained from the Sigma-Aldrich Corporation (Saint Louis, Mo.), except as noted. The oligomers were grown on about 0.1 grams of Rink amide resin (0.6 mmol/g, NOVABIOCHEM® available from EMD Chemicals Group, Merck KGaA, Darmstadt, Germany) that had been swelled and deprotected by the application of 20% 4-methylpiperidine (obtained from Alfa Aesar, Ward Hill, Mass.) in dimethyl formamide (DMF). The resin/oligomer was then bromoacylated by treatment with 1.2 M bromoacetic acid in DMF plus 0.95 eq neat or 3M diisopropylcarbodiimide (obtained from Advanced ChemTech, Louisville, Ky.) for 30 minutes with nitrogen bubbling. The resin/oligomer was then washed with 5 rinses in DMF after which a 1 M primary amine in DMF was added. This solution was again nitrogen bubbled for 100 minutes and similarly rinsed 5 times in DMF.

The amines used herein included R- or S-1-methylbenzylamine (available from Acros Organics, USA, Morris Plains, N.J.); 2-(t-butoxycarbamoyl)ethylamine, t-butyl D-, L-, or β-alanine, and t-butyl glycine (available from Chem-Impex International, Inc., Wood Dale, Ill.); and S-1-methyl-2-methoxyethylamine (Alfa). The amino acid esters were purchased as hydrochloride salts, and converted to free amines by dissolving in a minimal amount of dichloromethane, shaking with 0.95 eq 4M potassium hydroxide, drying the organic phase with brine and then anhydrous magnesium sulfate, followed by removal of the solvent, yielding a sometimes cloudy viscous oil that was dissolved in DMF.

Sulfur-containing moieties were added to the N-terminus of the peptoid oligomer by substituting methylthioacetic or thiolactic acid for bromoacetic acid in the acylation step, or by bromoacylation followed by displacement of bromide with 2-(methylthio)ethylamine. Oligomers were cleaved and deprotected by treating the resin with 4 mL 19:1 (v/v) trifluoroacetic acid (EMD Chemicals Group) and water. The solvent was evaporated, and the residue dissolved in 16 mL of a solution of 1:1 acetonitrile and water, filtered, and purified in 4 batches on a VYDAC® 10 μm, 22 mm×250 mm C4 column (available from W.R. Grace & Company, Columbia, Md.) using a 5%-95% water-acetonitrile gradient, both with 0.1% trifluoroacetic acid. Fractions corresponding to the main peak or peaks were collected and analyzed by LC-MS with a similar gradient using an Agilent 1100 Series LC/MSD Trap (XCT) high performance ion trap mass spectrometer (available from Agilent Technologies, Inc., Wilmington, Del.) and a VYDAC® C4 column, concentrated by vacuum centrifugation, and lyophilized.

Milligram batches of a peptoid were dissolved using at least 2 eq tris(hydroxymethyl)aminomethane and heated overnight at 60° C. This step is expected to aid folding the material into a stable conformation of the peptoid backbone, which involves slow cis-trans isomerization of the amide bonds. A typical stock solution was 0.67 mg/mL peptoid (about 0.34 mM for peptoid 1) in 100 mM pH 8.0 tris(hydroxymethyl)aminomethane (Tris).

Gold Particles: 5 nm and 10 nm aqueous colloidal gold and bis (p-sulfonato) triphenylphosphine were purchased from Sigma-Aldrich. These are prepared from 0.01 wt % $HAuCl_4$, from which we calculate a particle concentration of 76 nM for 5 nm particles, and 9.6 nM for 10 nm particles. Preparation of particles capped by this phosphine ligand and its functionalization with thiolated DNA followed the procedure described by Loweth, et al., ("DNA-Based Assembly of Gold Nanocrystals," *Angewandte Chemie International Edition*, 1999, v. 38 (12): 1808-1812), herein incorporated by reference, in its entirety, for all purposes. A DNA 100 mer 5'-functionalized with 6-hydroxyhexyl disulfide was purchased from Integrated DNA Technologies, Inc. (Coralville, Iowa) and dissolved in water at 0.1 mM without reduction of the disulfide. Assuming 100% yield, our stock solution of phosphine-protected, 5 nm gold particles was 1.0 µM. To functionalize these particles with DNA, 2 volumes of the gold stock solution was combined with 1 volume of DNA stock solution.

To cap particles with peptoids, 4 volumes of commercial colloidal gold was combined with 1 volume peptoid stock solution. Salt concentrations were adjusted using stock $MgCl_2$ solutions (60 mM for target concentrations of 10 mM, or 1M for higher concentrations) or solid sodium chloride, which was added by weight with the assumption that it adds volume according to its solid density. To add DNA to peptoid-protected particles, 20 µL DNA stock was added to 1.6 mL commercial 5 nm gold particles and incubated at room temperature for 5 hours. Then 0.4 mL peptoid stock was added, followed by overnight incubation. From this, we expect to have provided ratios of about 16 DNA oligomers and 1000 peptoids per particle. The particles were precipitated by adding brine or solid sodium chloride followed by centrifugation. After decanting, particles were resuspended in a mixture of 0.2 mL water and 16 or 32 µl, DNA stock, which provides another 13 or 26 DNA oligomers per particle. We estimate final concentrations of 540 nM gold particles and 7 or 14 µM DNA, some of which may be on particles.

Gel electrophoresis of peptoids and DNA was performed with 0.8% agarose gels (E-GEL®) obtained from Invitrogen Corporation, Carlsbad, Calif.) that use a proprietary TAE buffer system and ethidium bromide. The double-stranded DNA ladder was Invitrogen's E-GEL® 96 High-Range DNA Marker, ranging from 400 to 10,000 base pairs. Gels involving gold particles used 0.5×TBE and Sigma Ultrapure Agarose. Peptoids in gels were imaged using SIMPLYBLUE™ SafeStain (available from Invitrogen Corporation), following the product protocol.

Visible spectrometry was performed using a model UV-3802 split beam UV/Vis spectrophotometer with 1 mL PMMA cuvettes (available from UNICO, Inc., Dayton, N.J.). Dynamic light scattering from the same samples was measured using a Wyatt DAWN EOS Multi-Angle Light Scattering Spectrometer with QELS attachment (both available from Wyatt Technology, Santa Barbara, Calif.) at right angles to the beam path of the 690 nm laser. About 40 autocorrelation functions were measured for each sample. The measurements with the second, third, and fourth lowest initial values were averaged for the plots and the curves were normalized by their initial values for comparison. Circular dichroism spectra were recorded on a model J-815 Circular Dichroism Spectrometer (available from Jasco Inc., Easton, Md.) with peptoid stock solutions diluted with water. Transmission electron microscopy was performed on a JEOL model 2010F Transmission Electron Microscope (TEM, available from JEOL USA, Inc. Peabody, Mass.) with holey carbon grids (available from Ted Pella, Inc., Redding, Calif.) dipped into a gold particle sample.

Peptoid Sequence: Fernig et al., ("Rational and Combinatorial Design of Peptide Capping Ligands for Gold Nanoparticles," *Journal of the American Chemical Society*, 2004, v. 126 (32): 10076-10084) herein incorporated by reference, in its entirety, for all purposes, screened a library of short oligopeptides for tolerance of gold nanoparticles to high sodium chloride concentrations. The sequences CALNN and CCV-VVT were found to confer tolerance to hundreds of mM sodium chloride to these particles. These oligopeptides exhibit thiol and amine moieties on one end of the molecule, bulky hydrophobic spacers, and both neutral and anionic hydrophilic groups at the opposite end. We chose to include these features in our initial peptoid designs, the most successful of which are shown below in TABLE 1.

TABLE 1

Structures of Peptoids Studied in Detail

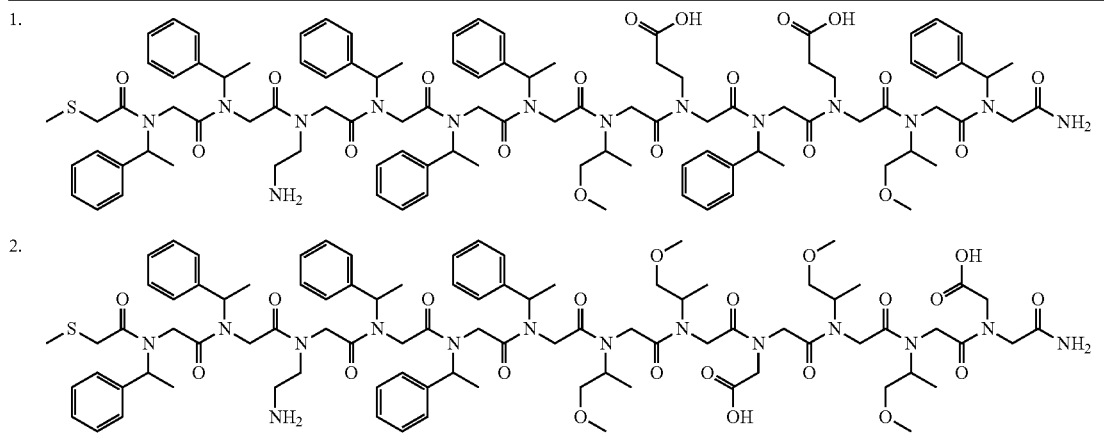

TABLE 1-continued

Structures of Peptoids Studied in Detail

3. 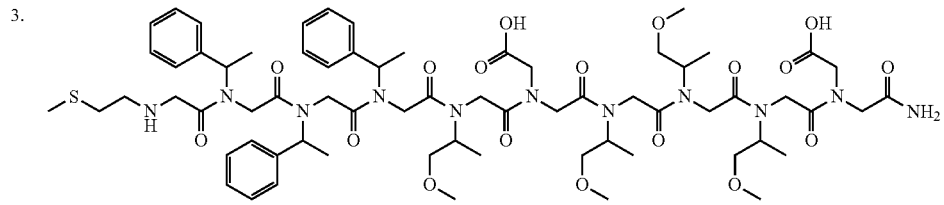

All methoxypropyl side-groups are S. For peptoid 1, all phenylethyl side-groups are R. For 2 and 3, all phenylethyl side-groups are S.

Each of peptoids 1-3 has a thioether at the N terminus, chosen because it can be incorporated in high yield with no protecting groups, and because it may be more easily displaced from the particle surface by a thiol-functionalized oligonucleotide or other useful molecule. An amine also appears near the N-terminus as a primary amine side-group in Peptoids 1 and 2, or as a secondary amine in the backbone in peptoid 3. Chiral R- or S-1-phenylethyl (rpe or spe) side-groups are bulky and hydrophobic, and are known to induce well defined helical conformations. Helicity is not thought to be essential for this application, but a well defined conformation can aid rationalization of sequence-property relationships, and may help form a compact region in a peptoid monolayer on a particle surface.

Hydrophilic groups appear near the C terminus. The C termini themselves are primary amides, and nearby side-groups include carboxylates and methyl ethers. Adjustment of the ratio of these side-groups allows tuning of charge. Peptoids 1-3 have a net charge of −1 at neutral pH. Peptoid 1 contains 1-phenylethyl side-groups in this segment that are expected to aid folding into a helical structure, based on a thorough conformational study of a water-soluble peptoid with a similar monomer sequence as shown by Sanborn, et al., ("Extreme Stability of Helices Formed by Water-Soluble Poly-N-Substituted Glycines (Polypeptoids) with α-Chiral Side Chains," *Biopolymers,* 2002, v. 63 (1): 12-20).

FIG. 1 shows circular dichroism spectra of the peptoids 1-3 described herein, showing features that are comparable in shape to the literature values for phenylethyl oligomers, and also comparable in magnitude for peptoids 1 and 2 (with opposite sign due to the opposite chirality used in the phenyl-ethyl side-groups). As might be expected, the shorter peptoid 3 shows a much weaker signal, indicating a less well defined helical conformation. Because the magnitudes of the per-monomer ellipticities (about $10^4$ deg cm$^2$/dmol) of peptoids 1 and 2 are comparable to the literature values, they apparently adopt a helical conformation over their entire length. The side-groups in the hydrophilic region o peptoid 2 are less bulky than those in peptoid 1 but the similarity of their spectra suggest a similar conformation, Based on the foregoing evidence, we believe that the following general structures shown below in TABLE 2 fall within the scope of this invention:

TABLE 2

General Chemical Structures of the Peptoids of Interest

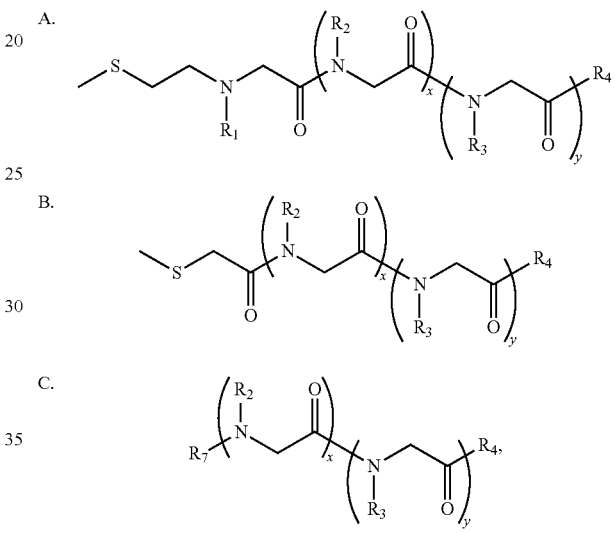

where x and y are 3-9; where $R_1$ is H, methyl, ethyl, or one of a branched and/or cyclic aliphatic or aromatic sidegroup with 3 to 20 carbons such as benzyl, 1-phenylethyl, 2-phenylethyl, hydrogenated forms of these, isopropyl, isobutyl, t-butyl, isoamyl, and 2-ethylhexyl; where $R_2$ is a combination with a majority of branched and/or cyclic aliphatic or aromatic side-groups with 3 to 20 carbons such as benzyl, 1-phenylethyl, 2-phenylethyl, hydrogenated forms of these, isopropyl, isobutyl, t-butyl, isoamyl, and 2-ethylhexyl, and preferably one or more aminoalkyl or aromatic amine-containing side-groups with 2 to 10 carbons such as 2-aminoethyl, 2-dimethylaminoethyl, 4-aminobutyl, 2-pyridylethyl, or 2-imidazolylethyl; where $R_3$ is a combination containing a minority of the sidegroups described for $R_2$ and a majority consisting of hydrophilic sidegroups with 2 to 10 carbons such as 2-methoxyethyl, 2-methoxy-1-methylethyl, carboxymethyl, 2-carboxyethyl, 2-carboxy-1-methylethyl, or 2-carboxamidoethyl; and where $R_4$ is OH, $NH_2$, or a group forming a secondary or tertiary amide, $NR_5R_6$, where $R_5$ and $R_6$ are a combination of H or groups with 1 to 8 carbons such as methyl, ethyl, or benzyl; and where $R_7$ is a group containing a moiety that is known in the art to bind strongly to a solid surface such as a thiol, thiolate, thiocarbamate, thioether, disulfide, isocyanate, catechol or similar phenolic moiety, or phosphonate, including such specific examples as lipoic acid, thiolactic acid, methylthioacetic acid, cysteine, methionine, oligocysteine, or oligohistidine bound as an amide to structure C, or a thioethyl, methylthioethyl, or phosphonoethyl group.

Figure 2A:
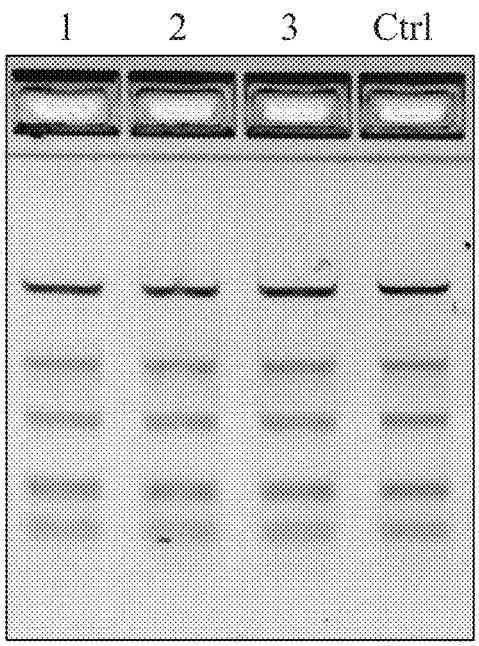
FIG. 2A shows the fluorescence response of ethidium bromide (also 3,8-Diamino-5-ethyl-6-phenylphenanthridinium bromide) bound to double-stranded DNA in the presence or absence (far right lane) of peptoid-DNA ladder mixtures of peptoids 1-3 in a 0.8% agarose gel electrophoresis in a TAE buffer, wherein the ladder bands are 0.4, 0.8, 2, 4, and 10 kilobase pairs, from bottom to top.
Figure 2B:
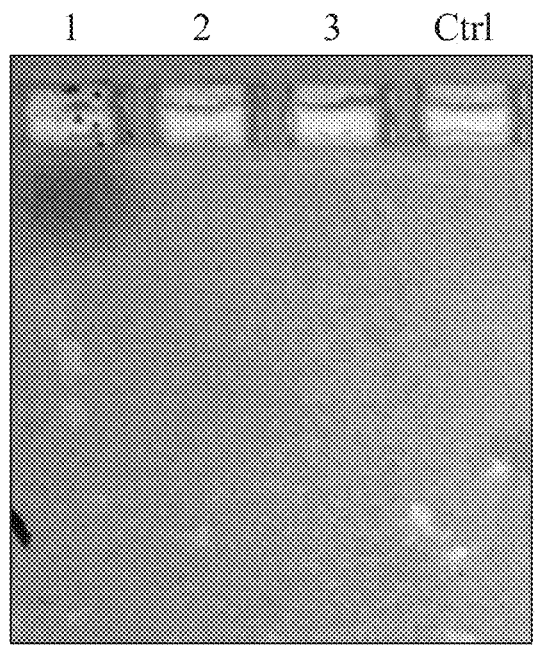
FIG. 2B shows Coomassie-stained peptoids in the same gel of FIG. 2A. A bovine serum albumin standard in the same gel was seen to stain darkly.

While peptoids with cationic and/or hydrophobic character have been shown to interact strongly with DNA, the peptoids described here do not. DNA with bound peptoids would have a different charge-to-mass ratio from free DNA, so its electrophoretic mobility should change. Ladders of double-stranded DNA exposed to peptoids 1-3 proceed unimpeded in gel electrophoresis, as shown in FIG. 2. Peptoids with hydrophobic character can be stained after the gel is run, and their transport is independent of that of the DNA, as illustrated in FIG. 2 in the case of peptoid 1, which is the most hydrophobic of the three peptoids; the others are not visible with this stain. We have seen that peptoids with more positively charged amine groups and fewer negatively charged carboxylate groups cause decreased mobility and smearing of DNA gel bands, or precipitation in the case of purely positively charged hydrophobic peptoids. Peptoids 1-3 have a net negative charge and are less hydrophobic than those in the prior work, and this has prevented their interaction with DNA.

DNA nanostructures involve several length scales of a few nanometers, such as that of a full turn of a DNA helix and the spacing between strands in DNA origami. To take full advantage of the spatial resolution of this technique for templating of inorganic material, particles should be about the same size. We have primarily focused on 5 nm gold particles, which are closest to this length scale among commercially available colloids. Aqueous synthesis of particles in this size range usually involves a combination of citric and tannic acids, which are expected to remain bound to the surface as demonstrated by Mühlpfordt ("The preparation of colloidal gold particles using tannic-acid as an additional reducing agent," *Experientia*, 1982, v. 38 (9): 1127-1128) and by Slot and Geuze ("A new method of preparing gold probes for multiple-labeling cyto-chemistry" *European Journal of Cell Biology*, 1985, v. 38 (1): 87-93) both herein incorporated by reference, in their entirety, for all purposes. The latter is a polyphenolic substance with a heterogeneous chemical structure that likely binds more strongly to the surface than citric acid. We seek a ligand exchange protocol that allows displacement of these with a more strongly binding peptoid, as well as separation of any excess or displaced ligands by precipitation of the particles or another simple method. This can have the additional advantage that the recovered particles can be more concentrated than before. For the water-soluble phosphine mentioned in the introduction, this is achieved by incubation of excess phosphine with the gold particles, followed by precipitation by raising the sodium chloride concentration to about 600 mM. The particles rely on electrostatic charge to avoid aggregation, but under high-salt conditions the charge is screened, allowing close contact between particles. Particles insufficiently substituted with phosphine cannot be redispersed in water, so dispersal indicates that some substitution has occurred. Peptoid 1-coated gold particles can be isolated by precipitation from 3M sodium chloride, but not peptoids 2 and 3. This shows that the peptoids 2 and 3 are extraordinarily effective at stabilizing the particles, but work against our need to concentrate them for imaging of their absorbance in a gel. However, the addition of trifluoroacetic acid to a final concentration of 80 mM protonates the carboxyl groups on the peptoids, reducing the charge on the particles and causing them to aggregate. Moreover, these can be resuspended in Tris borate buffer and form clear bands in a gel, as shown in FIG. 3A. A well defined trailing band, perhaps a dimer, also appears in each lane.

We desire the ability to selectively functionalize peptoid-protected particles by displacement with thiols, which in an application could be a 5'-mercaptohexyl DNA oligomer or a crosslinker between two templated particles with a low barrier to electron transport. As a preliminary demonstration of this, FIG. 3B shows a gel containing phosphine- and peptoid 1-treated gold particles, wherein the latter is subsequently treated with thioglycerol. The thioglycerol treatment causes aggregation that prevents most particles from entering the gel, a simple illustration that thiols can displace the peptoid. Moreover, peptoid 1-treated particles that are also treated with 3-mercaptopropionate migrate in a gel at the same rate as particles treated only with 3-mercaptopropionate, and at a different rate from particles treated only with peptoid 1 (see FIG. 3C), indicating that the thiol displaces the peptoid while keeping the particle stable under these conditions.

Figure 4:
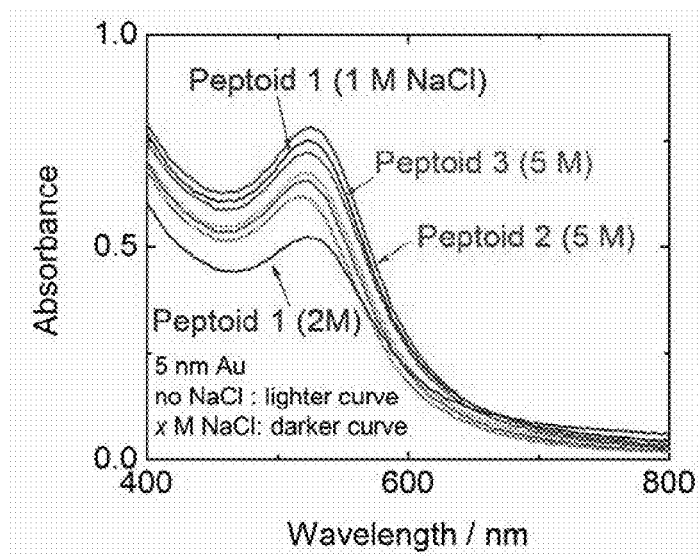
FIG. 4 shows the visible absorbance spectra of 5 nm gold particles (about 50 nM) and about 60 μM peptoids 1-3, with either no added sodium chloride or after 5 days in solution concentrations of 2M and 5M sodium chloride.

Monovalent salt tolerance: Colloidal gold particles are expected to aggregate in the presence of a sufficient ionic strength. Aggregation can be observed as precipitation, as a significant shift in the plasmon peak, or as changes in the timescale of fluctuations in scattered light intensity. When saturated aqueous sodium chloride is added to bring its concentration to 600 mM in the presence of phosphine-protected gold particles, the particles aggregate upon mixing (as observed by a darkening or loss of red color) and then precipitate. The visible spectra of these particles record the surface plasmon peak, which red shifts and decreases when particles aggregate. As shown in FIG. 4 peptoid-1 protected particles were exposed to high concentrations of sodium chloride by adding the solid salt. No peak shift is observed when the salt concentration is 1 M. At 2 M, the solution initially became cloudy, and after several days became clear with a reduced absorbance. As noted above, precipitation is observed at 3 M.

Figure 5A:
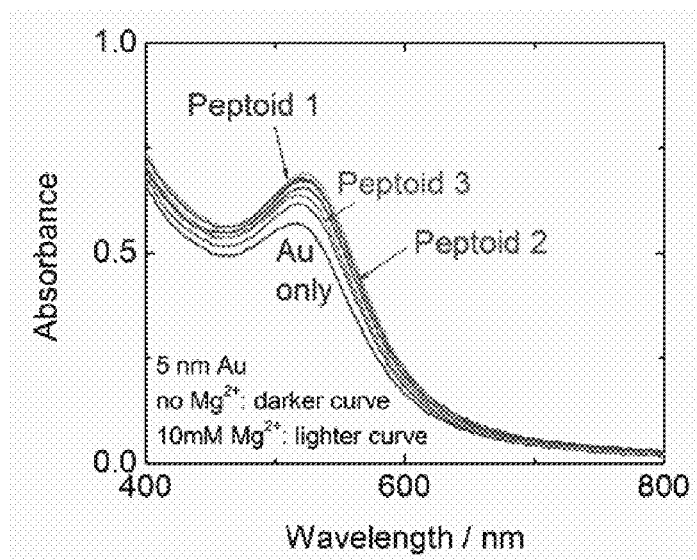
FIG. 5A shows the visible absorbance spectra of (1) untreated 5 nm gold particles at a concentration of about 50 nM in 16 mM pH 8.0 tris(hydroxymethyl)aminomethane (Tris); and (2) 5 nm gold particles treated with about 60 μM of one of peptoids 1, 2 or 3 in aqueous solutions with and without 10 mM magnesium chloride.

Peptoids 2 and 3 showed no significant peak shift after 5 days even in 5 M sodium chloride. Only partial precipitation, with no color change, was observed after centrifugation (16,000 g, for 10 min) in a saturated solution in the presence of solid salt. FIG. 5A shows that plasmon peaks have not shifted at these upper limits.

Figure 5B:
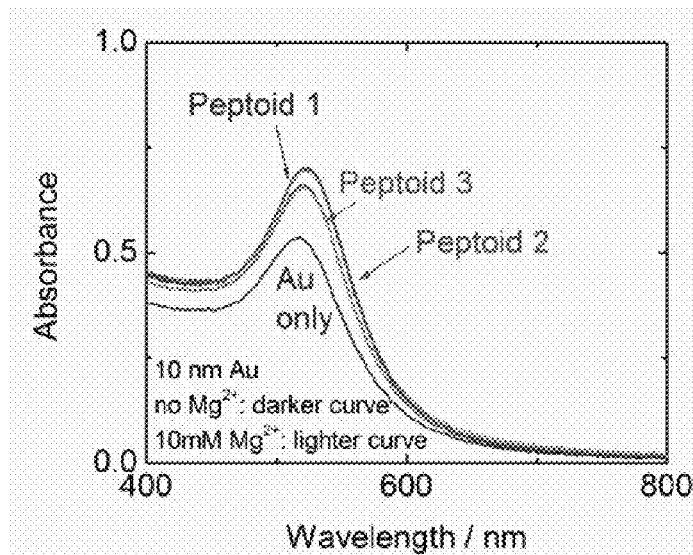
FIG. 5B shows the visible absorbance spectra of (1) untreated 10 nm gold particles at concentrations of about 6 nM in water; and (2) 10 nm gold particles treated with about 60 μM of one of peptoids 1, 2 or 3 in aqueous solutions with and without 10 mM magnesium chloride.
Figure 6A:
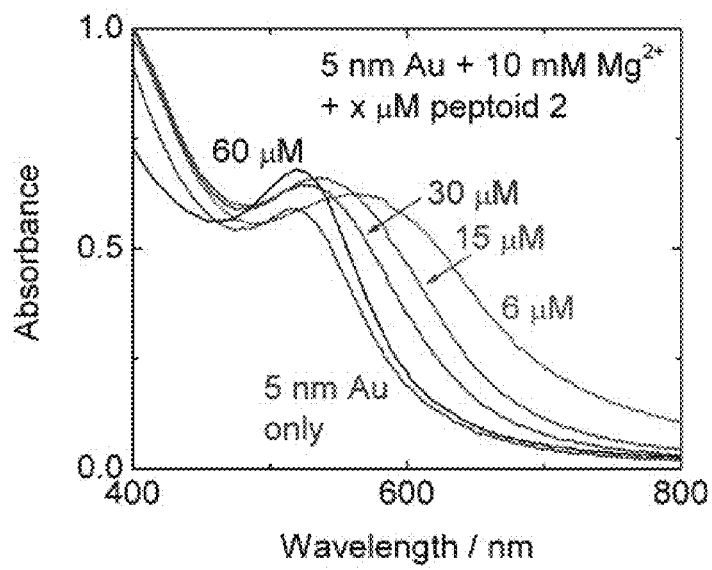
FIG. 6A shows the visible absorbance spectra of (1) untreated 5 nm gold particles at concentrations of about 50 nM, and (2) 5 nm gold particles treated with concentrations of peptoid 2 of 6, 15, 30 and 60 nM, in 10 mM constant concentration aqueous solutions of magnesium chloride, each measured 5 minutes after preparation.
Figure 6B:
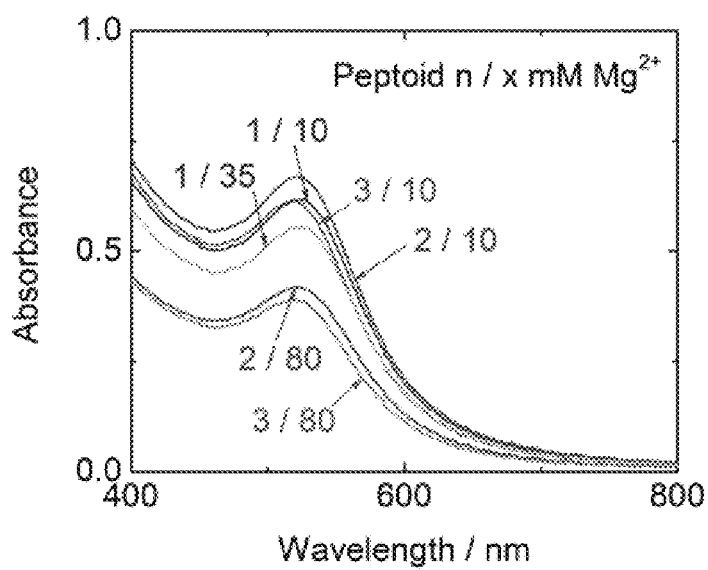
FIG. 6B shows the effect on the visible absorbance spectra the solutions of treated gold particles shown in FIG. 4B that result from increased magnesium chloride concentration of 35 mM (peptoid 1) and 80 mM (peptoids 2 and 3). The decrease in peak height is primarily due to dilution.
Figure 7A:
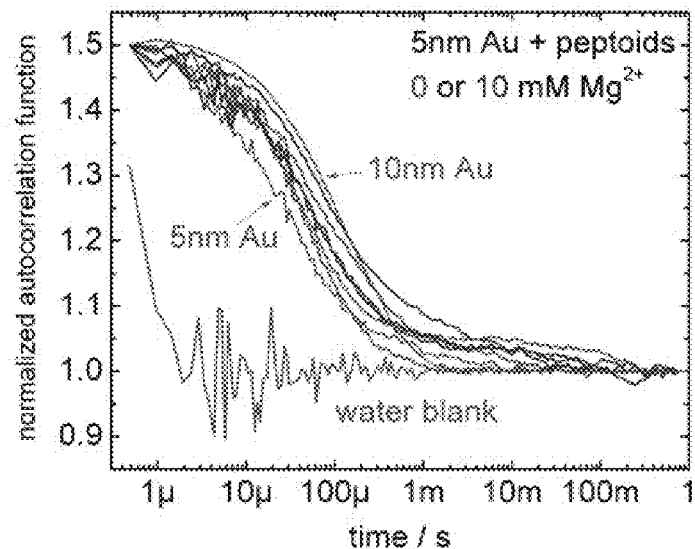
FIGS. 7A and 7B show normalized dynamic light scattering traces of the samples shown in FIGS. 5A and 5B. The water blank is not normalized.
Figure 7B:
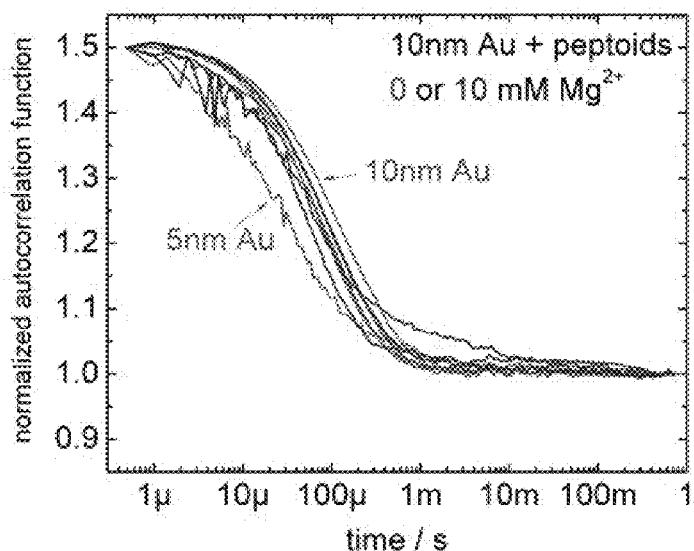
Figure 7C:
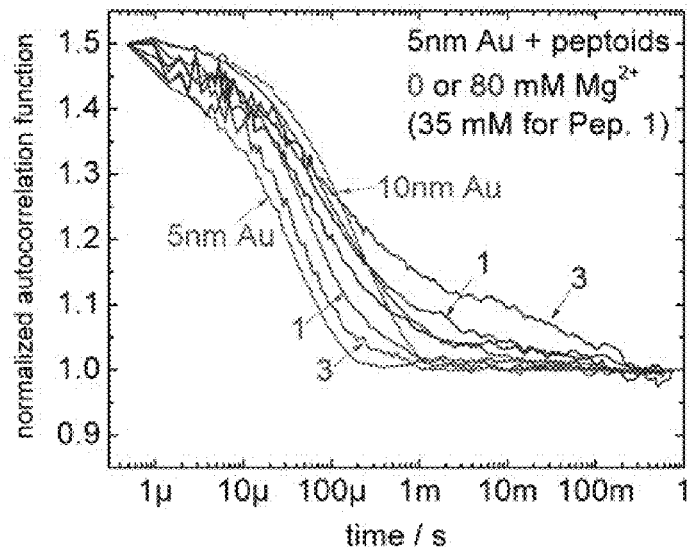
FIGS. 7C and 7D show normalized dynamic light scattering traces of the samples shown in FIGS. 6A and 6B and similarly treated 10 nm particles.
Figure 7D:
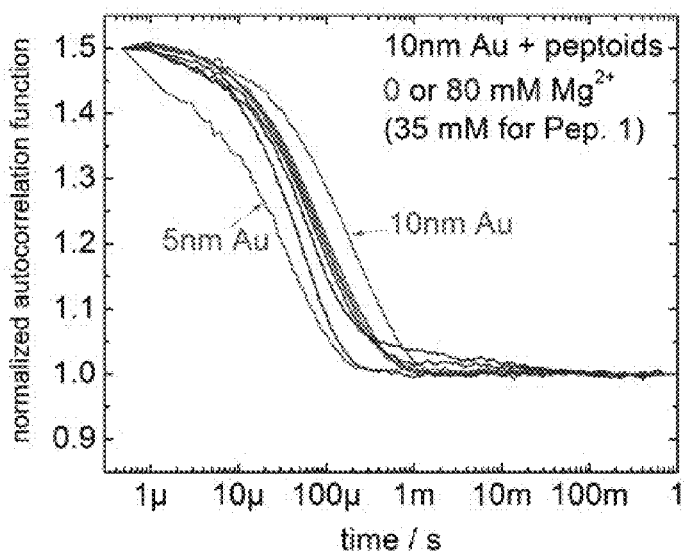

Divalent salt tolerance: The extreme monovalent salt tolerance afforded by peptoids 2 and 3 may actually be a disadvantage because it precludes a method to concentrate or isolate the particles. In contrast, tolerance to divalent salt is advantageous because it allows use of gold nanoparticles with biomolecules requiring it. When magnesium chloride is added from a 60 mM stock solution to bring its concentration to 2 mM in the presence of phosphine-protected gold particles, the particles darken upon mixing for 1 min and then slowly precipitate. However, peptoid-protected particles show no significant absorbance peak shift at fivefold higher concentration, as shown in FIGS. 5A and 5B for both 5 nm and 10 nm particles. In fact, Peptoid 1-treated 5 nm gold does not lose its red color until the magnesium ion concentration is raised to 35 mM, and is stable at 20 mM. Peptoids 2 and 3 are stable at 80 mM but not 160 mM. FIG. 6B shows that plasmon peaks have not shifted at these upper limits.

From the concentrations calculated in the section headings "Peptoid Synthesis" and "Gold Particles" above, and assuming 5 adsorbates/$nm^2$, 30 µM peptoid will adsorb onto the surfaces of 50 nM, 5 nm particles, and 15 µM peptoid will adsorb onto 6 nM, 10 nm particles; the absorbate density is based on Chidsey et al., ("Chemical Functionality in Self-Assembled Monolayers Structural and Electrochemical Properties," *Langmuir*, 1990, v. 6 (3): 682-691). FIG. 6A shows that, if the peptoid concentration is at or below this in the 5 nm case, protection against magnesium is lost. At the lower concentrations, the particles are not completely coated by peptoids and can be expected to be more prone to aggregation. Peptoids are able to protect particles without requiring a significant excess of free peptoid, so they are apparently forming stable surface layers.

The plasmon peak of colloidal gold is sensitive to factors other than the state of aggregation (such as the identity of surface ligands). Dynamic light scattering provides an independent and more sensitive indication of particle aggregation. Fluctuations in the intensity of scattered light provide a measure of the timescale of particle diffusion, expected to be longer for larger particles or particle aggregates. The technique is most sensitive to the largest aggregates present. We used commercial 5 and 10 nm gold particles as standards, and then examined the samples presented in FIGS. 5A and 5B. The autocorrelation functions for both sizes of peptoid-treated particles shown in FIGS. 7A-7D fell between those of the standards, regardless of the presence of 10 mM magnesium chloride. This provides further evidence that there is no significant aggregation of the particles under these conditions.

At higher magnesium concentrations, the 10 nm particles are unaffected. The curves for 5 nm particles suggest a small population of aggregates larger than 10 nm that are probably formed reversibly, given that the colloids remain stable on a timescale of weeks. Dynamic light scattering is more sensitive to the presence of aggregates than the absorbance spectrum, so it is no surprise that this phenomenon is observed even though no peak shift is observed in FIG. 6B.

We have also observed by light scattering and spectrometry that peptoid-protected particles confer stability against 10 mM magnesium ion even at elevated temperatures. Particles with peptoids 1 and 2 were stable to a one hour exposure to 94° C. Those with peptoid 3 were not, but withstood 1 hour at 65° C. Since these are conditions similar to those used in the assembly of DNA nanostructures, it may be possible to incorporate particles into these structures during that step instead of in a separate post-assembly step. The reduced thermal stability of peptoid 3 suggests that it may constitute a practical lower bound on peptoid length.

Figure 8A:
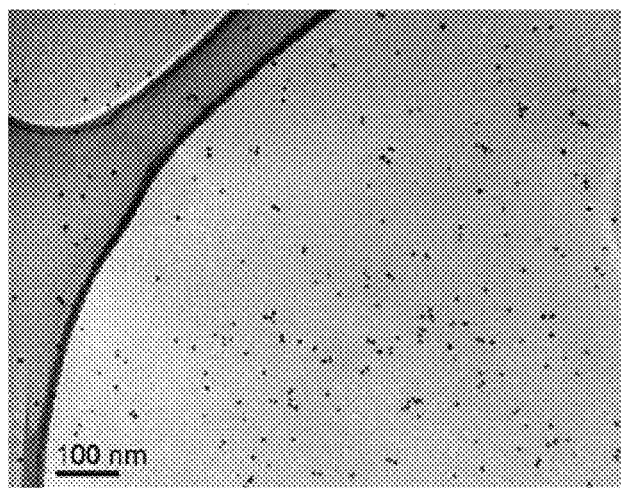
FIG. 8A shows a transmission electron micrograph of grids dipped in 5 nm gold particle samples treated with peptoid 2 and 10 mM magnesium chloride.
Figure 8B:
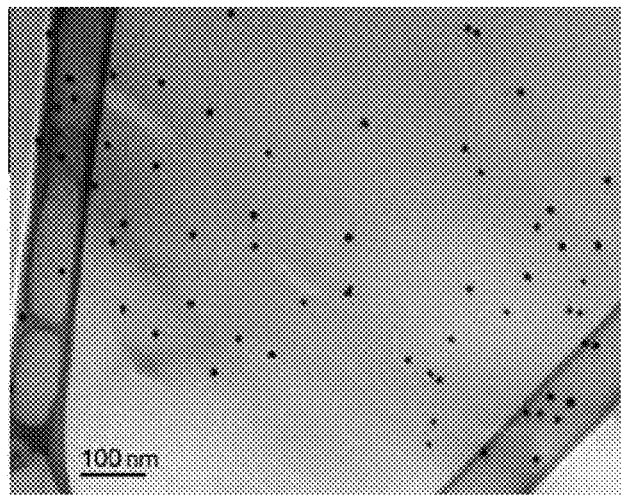
FIG. 8B shows a transmission electron micrograph of grids dipped in 10 nm gold particle samples treated with peptoid 2 and 10 mM magnesium chloride.
Figure 8C:
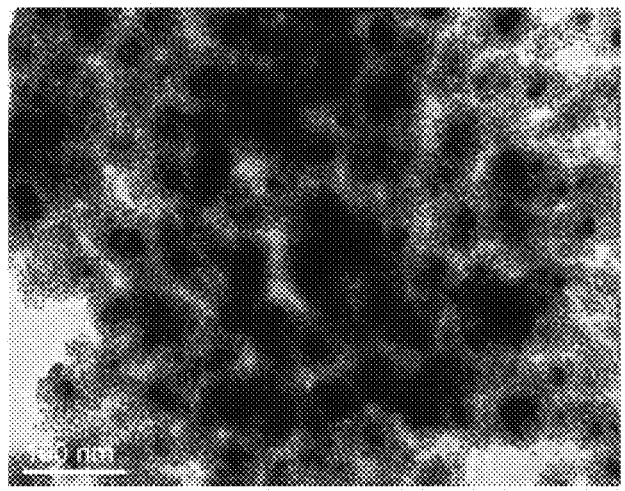
FIG. 8C shows a transmission electron micrograph of phosphine-protected 5 nm gold in 20 mM magnesium chloride.

The assertion that the particles are freely dispersed in the 10 mM $Mg^{+2}$ samples is further justified by transmission electron microscopy. In FIGS. 8A-8C, grids dipped in the peptoid 2-protected 5 and 10 nm samples show a significant population of isolated particles bound to the grid. Some two-dimensional aggregates are present, which commonly occurs upon drying of a sufficiently concentrated solution onto the grid. In contrast, phosphine-coated 5 nm particles exposed to 20 mM $Mg^{+2}$ form a mixture of two- and three-dimensional aggregates on the grid, with few isolated particles. We believe that loosely bound three-dimensional aggregates exist in solution that partially spread out when they are deposited onto the grid. In such loose aggregates, we expect that the phosphine coating is still on the particles, and few particles form metallic bonds, but they are electrostatically bound together by the divalent ion.

Aqueous gold nanoparticles generally have a net negative charge, due to their surface ligands and/or to charge on the metal. Divalent salt is expected to at least occasionally attract a pair of particles into very close proximity, overcoming their mutual electrostatic repulsion and increasing the likelihood that they will form larger aggregates and other types of chemical bonds. If their surface ligands are fluxional or incompletely cover the surface, their high-energy metal surfaces can make contact, likely resulting in irreversible metallic bond formation. The higher curvature of smaller particles gives them higher surface energy and more heterogeneous arrangements of surface coordination sites, and makes inter-ligand interaction less likely, so it is not surprising that we could stabilize 10 nm particles in a broader range of conditions than possible for 5 nm particles. The presence of a bulky hydrophobic region in a ligand can help cover the surface, and also stabilize ligands on the surface by interaction with neighboring ligands. The outer carboxyl groups on the peptoids add negative charge to aid electrostatic repulsion between particles, and they and the neutral hydrophilic groups contribute to water solubility. However, too much negative charge may increase interaction with magnesium or compact DNA structures. Intermingling bulky hydrophobic groups in the outer region appear detrimental to stabilization of particles, although in the case of peptoid 1, this has worked to our advantage by providing a high-yield method to concentrate the particles. The ability to easily adjust peptoid sequence allows for efficient screening of structure-property relationships. While this does not provide complete answers, it provides patterns yielding many clues to the mechanism of particle stabilization.

Figure 9:
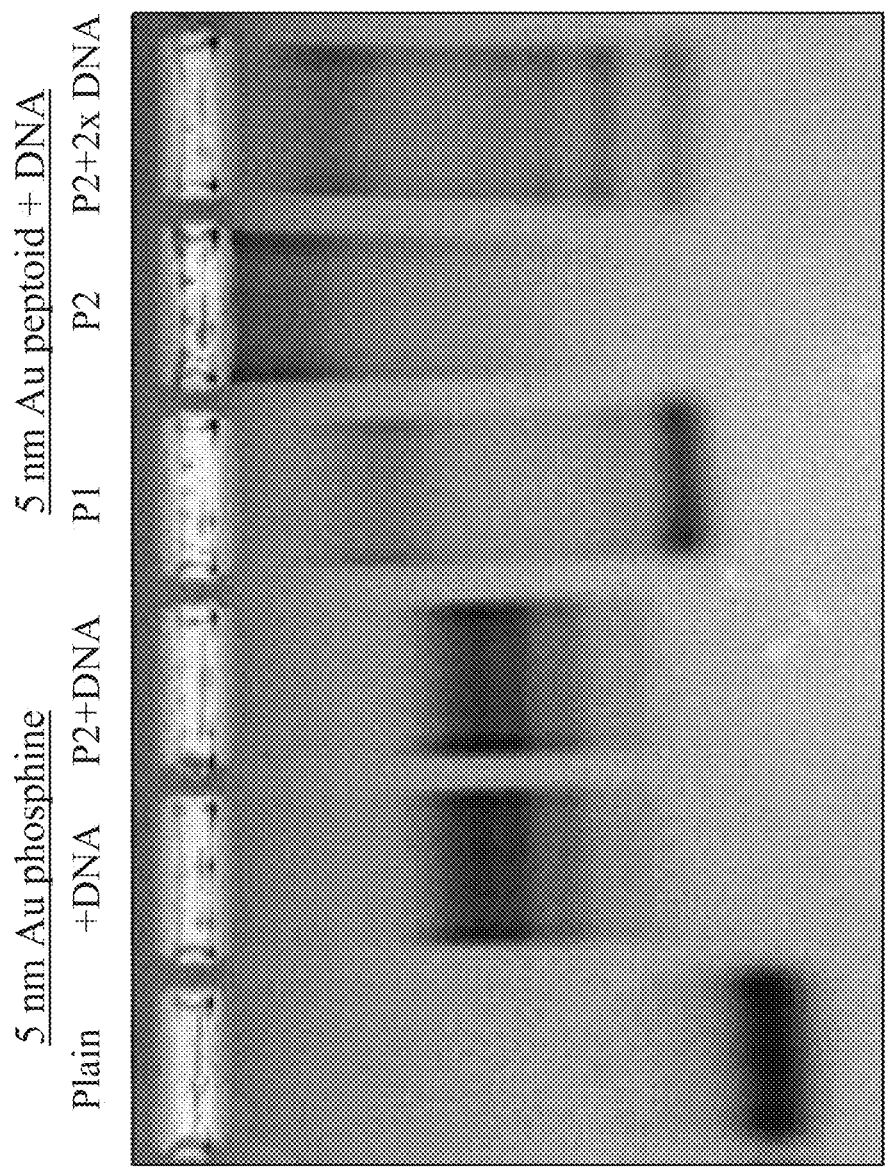
FIG. 9 shows a comparison of electrophoresis of treated 5 nm gold particles in 2% agarose gel, 0.5×TBE buffer, wherein the lane labeled "Plain" comprises phosphine-protected gold without DNA; the lane labeled "+DNA" comprises phosphine-protected gold with DNA; the lane labeled "P2+DNA" comprises phosphine-protected gold with DNA and peptoid 2; the lane labeled "P1" comprises peptoid 1-protected gold; the lane labeled "P2" comprises peptoid 2-protected gold; and the lane labeled "P1+DNA" comprises peptoid 1-protected gold with DNA. All particles were concentrated by salt precipitation.

DNA functionalization: Peptoid 1-protected 5 nm gold particles can be functionalized with one or a few thiolated DNA oligomers in much the same way as has been demonstrated in the literature for phosphine-protected gold (e.g. Zanchet, et al., "Electrophoretic Isolation of Discrete Au Nanocrystal/DNA Conjugates," Nano Letters, 2001, v. 1 (1): 32-35, herein incorporated by reference in its entirety for all purposes). It may also work with peptoids 2 and 3, but we have not yet demonstrated this aspect using particles concentrated enough to be observable by absorbance in a gel. FIG. 9 shows a comparison of the phosphine-treated particles (left 3 lanes) with peptoid-treated particles (right 3 lanes). Surface binding of a small number of thiolated DNA 100 mers produces a series of bands corresponding to increasing numbers of oligomers. This process is not efficient; we use an approximately 40-fold excess here. It has been shown that the individual bands of DNA-substituted phosphine-coated particles can be extracted from the gel and used for other purposes; other separation methods have been developed (such as those described by Claridge et al., ("Isolation of Discrete Nanoparticle-DNA Conjugates for Plasmonic Applications," Nano Letters, 2008, v. 8 (4): 1202-1206). We incubated the particles at room temperature for several hours first with sub-monolayer amounts of disulfide-functionalized DNA (as received, and not deprotected to a thiol) and then with peptoid for several hours each, likely forming a mixed coating of DNA and peptoid on the surfaces of particles. These can be concentrated by adding solid sodium chloride, even when peptoid 2 is used. The DNA may not stay on the particle during precipitation and resuspension, because we found it necessary to add more DNA to obtain discrete gel bands using peptoid 1. However, we have not obtained discrete bands with peptoid 2. We think this is because they do not form mixed monolayers with DNA in the same proportions as Peptoid 1; perhaps with further optimization this will be more successful.

The distinction between thiolated and disulfide-functionalized DNA is subtle in our case. Previous work indicates that disulfides result in adsorbates on gold that are indistinguishable from those prepared with thiols; a surface-induced reduction apparently occurs (Bain, et al., "Comparison of Self-Assembled Monolayers on Gold: Coadsorption of Thiols and Disulfides," Langmuir, 1989, v. 5 (3): 723-727; and Porter, et al., "Gold and Silver Nanoparticles Functionalized by the Adsorption of Dialkyl Disulfides," Langmuir, 1998, v. 14 (26): 7378-7386). However, it was seen that disulfides adsorb less readily than thiols. This may actually be useful when forming mixed monolayers with thioether-containing peptoids, which probably also adsorb less readily. Agents used to reduce disulfides can competitively adsorb onto gold, product can be lost during purification, and the thiol has a shorter shelf life; so there are benefits if the disulfide can be used directly without a prior reduction step. However, further work may show that the need for excess DNA can be avoided if it is reduced prior to use.

Therefore, short peptides of the proper sequence can bind to the surface of gold nanoparticles and stabilize them in the presence of high concentrations of monovalent salt, and moderate concentrations of divalent salt, both much higher than have been previously demonstrated. They allow creation of particles with low ligand-to-inorganic core volume ratios that are stable enough for nucleic acid nanostructures, and for biological labeling, targeting, and delivery applications. The peptoid-coated particles can be precisely functionalized with nucleic acids, illustrating a useful degree of versatility. The combination of precise and modular synthetic control and the robust conformational properties of peptoids make them a useful platform for optimization of properties and understanding of their performance mechanisms. These are likely to make peptoids a compelling approach to the design and application of interfaces between biological systems and inorganic nanomaterials.

Finally, we believe that this process is applicable not only to gold nanoparticles but also to nanoparticles of other noble metals such as silver, platinum, palladium and mercury as well as alloys of any combination of gold, silver, platinum, palladium and mercury metals. Moreover, the same would be true for nanoparticles coated partially or completely with a layer of any of these metals or metal alloys. Furthermore, materials to which organo-sulfur groups will bind at the surface, such as zinc sulfide, cadmium sulfide, zinc selenide, cadmium selenide, and zinc telluride, may also be protected with peptoids and functionalized with a few or several thiolated DNA oligomers in the manner described above. Phosphonate and catecholate groups are known to bind strongly to metal oxide or ceramic nanoparticles and are possible to incorporate at the N terminus of a peptoid. The literature shows clearly that nanoparticle surface ligands can confer stability over a wide range of particle sizes and shapes; for example, gold nanoparticles formed by the citrate-tannic acid process span a range from 3 nm to 150 nm (op. cit. Slot and Geuze; and Frens, G. "Controlled Nucleation for Regulation of Particle Size in Monodisperse Gold Suspensions," *Nature-Physical Science*, 1973, v. 241 (105): pp. 20-22) and nanorods with similar surface chemistry can be formed with high aspect ratio (Jana, N. R.; Gearheart, L.; Murphy, C. J, "Wet chemical synthesis of high aspect ratio cylindrical gold nanorods," *Journal of Physical Chemistry B*, 2001, v. 105 (19): pp 4065-4067), both of which are herein incorporated by reference. Because the present invention begins with a similar surface chemistry that has been demonstrated with a multiplicity of particle sizes and shapes, we expect that our materials will likewise perform over a similarly broad range of particle size and shape in a manner that similar to what we have already demonstrated.

Therefore, having thus described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

Finally, to the extent necessary to understand or complete the disclosure of the present invention, all publications, patents, and patent applications mentioned herein are expressly incorporated by reference therein to the same extent as though each were individually so incorporated.

What is claimed is:

1. A peptoid compound, represented by the formula comprising:

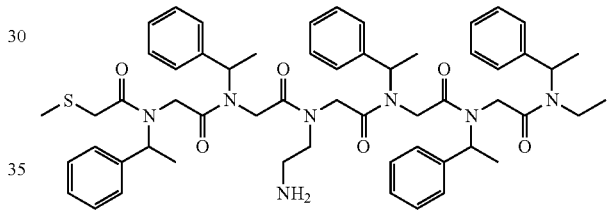

2. A peptoid compound, represented by the formula comprising:

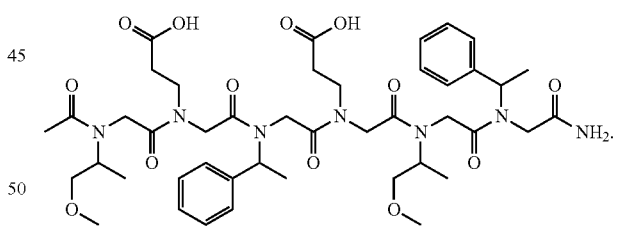

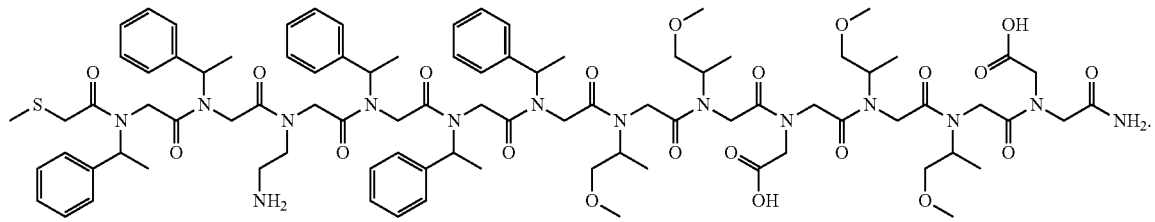 [SMILES: COCC(C)N(CC(=O)N(CC(N)=O)CC(=O)O)C(=O)CN(C(=O)CN(CC(=O)O)C(=O)CN(C(=O)CN(C(=O)CN(C(=O)CN(C(=O)CN(C(=O)CN(CCN)C(=O)CN(C(=O)CN(C(=O)CSC)C(C)c1ccccc1)C(C)c1ccccc1)C(C)c1ccccc1)C(C)c1ccccc1)C(C)c1ccccc1)C(C)COC)C(C)COC)C(C)COC]

3. A peptoid compound, represented by the formula comprising:
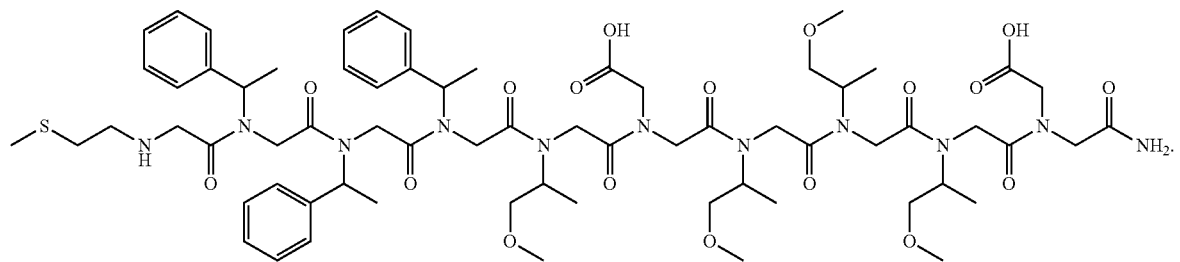 [SMILES: COCC(C)N(CC(=O)N(CC(N)=O)CC(=O)O)C(=O)CN(C(=O)CN(C(=O)CN(CC(=O)O)C(=O)CN(C(=O)CN(C(=O)CN(C(=O)CN(C(=O)CNCCSC)C(C)c1ccccc1)C(C)c1ccccc1)C(C)c1ccccc1)C(C)COC)C(C)COC)C(C)COC]
* * * * *